United States Patent
Huang et al.

(10) Patent No.: US 10,436,753 B2
(45) Date of Patent: Oct. 8, 2019

(54) METHOD AND DEVICE FOR ADJUSTING ARRAY STRUCTURE OF OMNIDIRECTIONAL ELECTROMAGNETIC ACOUSTIC TRANSDUCERS FOR IMAGING DEFECT PROFILE OF METAL PLATE

(71) Applicants: Nanchang Hangkong University, Nanchang (CN); Tsinghua University, Beijing (CN)

(72) Inventors: Songling Huang, Beijing (CN); Kai Song, Nanchang (CN); Wei Zhao, Beijing (CN); Chao Lu, Nanchang (CN); Yu Zhang, Beijing (CN); Shen Wang, Beijing (CN); Zhe Wang, Beijing (CN)

(73) Assignees: NANCHANG HANGKONG UNIVERSITY, Nanchang (CN); TSINGHUA UNIVERSITY, Beijing (CN)

( * ) Notice: Subject to any disclaimer, the term of this patent is extended or adjusted under 35 U.S.C. 154(b) by 162 days.

(21) Appl. No.: 15/862,771

(22) Filed: Jan. 5, 2018

(65) Prior Publication Data
US 2018/0231504 A1    Aug. 16, 2018

(30) Foreign Application Priority Data
Feb. 14, 2017    (CN) .......................... 2017 1 0078895

(51) Int. Cl.
*G01N 29/06*    (2006.01)
*G01N 29/11*    (2006.01)
(Continued)

(52) U.S. Cl.
CPC ....... *G01N 29/2412* (2013.01); *G01N 29/069* (2013.01); *G01N 29/0672* (2013.01);
(Continued)

(58) Field of Classification Search
CPC .......... G01N 29/4427; G01N 29/0672; G01N 29/069; G01N 29/11; G01N 29/07;
(Continued)

(56) References Cited

U.S. PATENT DOCUMENTS 5,808,202 A * 9/1998 Passarelli, Jr. ..... G01N 29/2412
  702/36
6,502,463 B1 * 1/2003 Clark ........................ G01L 1/12
  73/597

(Continued)

FOREIGN PATENT DOCUMENTS

CN         105044220        * 11/2015 ............. G01N 29/34

*Primary Examiner* — Jacques M Saint Surin
(74) *Attorney, Agent, or Firm* — Hodgson Russ LLP

(57) ABSTRACT

A method for adjusting array of omnidirectional EMATs includes: uniformly arranging N EMATs in a detection region of a metal plate; calculating positions of scattering points according to amplitudes and travel times of guided wave scattering signals, and forming a first defect profile curve by performing three smooth spline interpolations on coordinate data of positions of scattering points; calculating curvatures of points on the first defect profile curve by solving a first and second derivatives of a function of the first defect profile curve; determining an array adjustment region by comparing the curvature with a preset threshold, adjusting the array and calculating a second defect profile curve; and performing data fusion on the first and second defect profile curves to form a defect profile image of the metal plate.

11 Claims, 3 Drawing Sheets

(51) Int. Cl.
*G01N 29/07* (2006.01)
*G01N 29/44* (2006.01)
*G01N 29/24* (2006.01)

(52) U.S. Cl.
CPC ............. *G01N 29/07* (2013.01); *G01N 29/11* (2013.01); *G01N 29/4427* (2013.01); *G01N 2291/0425* (2013.01); *G01N 2291/106* (2013.01)

(58) Field of Classification Search
CPC ....... G01N 29/2412; G01N 2291/0425; G01N 2291/106
USPC .......................................................... 73/628
See application file for complete search history.

(56) References Cited

U.S. PATENT DOCUMENTS

| | | | |
|---|---|---|---|
| 7,426,867 B2* | 9/2008 | Koch | B06B 1/04 |
| | | | 324/226 |
| 7,578,166 B2* | 8/2009 | Ethridge | G01N 29/07 |
| | | | 73/1.82 |
| 7,997,139 B2* | 8/2011 | Owens | G01N 29/2412 |
| | | | 702/39 |
| 9,488,623 B2* | 11/2016 | Rose | G01N 29/34 |
| 9,638,671 B2* | 5/2017 | Borigo | G01N 29/2412 |
| 2018/0059065 A1* | 3/2018 | Hull | G01J 5/10 |

* cited by examiner

METHOD AND DEVICE FOR ADJUSTING ARRAY STRUCTURE OF OMNIDIRECTIONAL ELECTROMAGNETIC ACOUSTIC TRANSDUCERS FOR IMAGING DEFECT PROFILE OF METAL PLATE

CROSS-REFERENCE TO RELATED APPLICATION

This application claims priority to and benefits of Chinese Patent Application Serial No. 201710078895.4, filed with the State Intellectual Property Office of P. R. China on Feb. 14, 2017, the entire content of which is incorporated herein by reference.

FIELD

The present disclosure relates to the field of non-destructive detection, and especially to a method and device for adjusting an array structure of omnidirectional electromagnetic acoustic transducers (EMATs) for imaging a defect profile of a metal plate.

BACKGROUND

Generally, in a process for detecting a metal plate, it is only possible to judge whether a defect is present and to determine its position if it is present in most case. However, it is more important to obtain quantitative information (such as a size and a profile) of the defect of the metal plate, which can be used as an important basis for evaluating a health status of the metal plate and guiding the reparation and maintenance of the metal plate.

With increasingly strict requirements on the safety of the metal plate, there are needs to determine the profile shape of the defect, to image the defect with high precision, and to visualize a detection result of the defect.

In the related art, an ultrasonic guided wave has the following features: low attenuation, far propagation distance, 100% coverage of the thickness of the metal plate by a sound field, easy adjustment of a guided wave mode, etc. Moreover, detection with guided waves of omnidirectional electromagnetic acoustic transducers for an area surrounded by the transducer array from multiple angles can provide more abundant and accurate defect information for high-precision imaging of the defect.

However, a strong degree of scattering occurs when the guided wave encounters the defect, which will cause more artifacts in a defect image re-established by a guided wave imaging method in the related art, resulting in blind detection regions and seriously affecting location and imaging accuracy of the defects of the metal material. In addition, a transducer array in a specific geometric structure only has a best matching-degree and sensitivity to a defect having the specific scattering feature. However, an actual defect is very complex, and shape and scattering characteristics thereof are varied, therefore, a serious mismatch is present between the transducer array in the specific geometric structure and the actual complex defect with varied scattering characteristics, and the transducer array in the specific geometric structure cannot always maintain a high sensitivity to the actual complex defect, thereby resulting in a limited detection and imaging precision to the actual defect.

At present, the array structure for detection is relative fixed and regular, there are few studies on the relationship between the array structure and the defect imaging accuracy, and there is no research on the dynamic adjustment and performance optimization of the geometric topology structure of the transducer array.

SUMMARY

The present disclosure seeks to solve at least one of the problems that exist in the related art to at least some extent.

According to an embodiment of a first aspect of the present disclosure, a method for adjusting an array structure of omnidirectional electromagnetic acoustic transducers for imaging a defect profile of a metal plate is provided, the method includes:

uniformly arranging N omnidirectional electromagnetic acoustic transducers in a detection region of the metal plate to be detected, in which each of the omnidirectional electromagnetic acoustic transducers is used as an omnidirectionally emitting electromagnetic acoustic transducer to excite an omnidirectional ultrasonic guided wave in a certain order, and used as an omnidirectionally receiving electromagnetic acoustic transducer to omnidirectionally receive a guided wave scattering signal of a defect when an ultrasonic guided wave is present in the detection region of the metal plate to be detected;

calculating a position of a scattering point according to an amplitude and travel time of the guided wave scattering signal of the defect, and forming a first defect profile curve by performing three smooth spline interpolations on coordinate data of the position of the scattering point;

calculating a curvature of each point on the first defect profile curve in a planar polar coordinate system by solving a first derivative and a second derivative of a function of the first defect profile curve;

determining an array adjustment region by comparing the curvature of the each point with a preset curvature threshold, adjusting the array structure according to the array adjustment region, and calculating a second defect profile curve of the guided wave scattering signal of the defect; and performing data fusion on the first defect profile curve and the second defect profile curve so as to form a defect profile image of the metal plate to be detected.

In an embodiment of the present disclosure, calculating a position of a scattering point according to an amplitude and travel time of the guided wave scattering signal of the defect, and forming a first defect profile curve by performing three smooth spline interpolations on coordinate data of the position of the scattering point includes:

establishing the planar polar coordinate system, and calculating the position of the scattering point by following formulas:

$$|\vec{TP}| + |\vec{PR}| = v * t_r$$

$$A * \frac{1}{\sqrt{|\vec{TP}|}} * a_s * \frac{1}{\sqrt{|\vec{PR}|}} = A_{RS},$$

where $t_r$ is an actually measured travel time of the guided wave scattering signal of the defect, $v$ is a propagation velocity of the guided wave scattering signal of the defect in the metal plate, $T$ is a position of the omnidirectionally emitting electromagnetic acoustic transducer, $R$ is a position of the omnidirectionally receiving electromagnetic acoustic transducer, $A$ is a signal intensity of the omnidirectional ultrasonic guided wave excited at the position $T$ of the omnidirectionally emitting electromagnetic acoustic transducer, $a_s$ is a scattering attenuation coefficient of the signal intensity when the ultrasonic guided wave is scattered, and $A_{RS}$ is an intensity of the guided wave scattering signal of the defect received at the position R of the omnidirectionally receiving electromagnetic acoustic transducer; and performing three smooth spline interpolations on polar coordinates $P_i(\theta_i, r_i)$ of S scattering points obtained to form the first defect profile curve and a function $PC(\theta_j, r_j)$ thereof, where S is a positive integer, and $P_i(\theta_i, r_i)$ is the polar coordinate of the scattering point, where i=1, 2, . . . , S, $PC(\theta_j, r_j) = CSplineI[P_i(\theta_i, r_i)]$ where j=1, 2, . . . , S1, and S1 is a positive integer and represents a total number of the points on the first defect profile curve, CSplineI is a function for performing three smooth spline interpolations on the polar coordinate $P_i(\theta_i, r_i)$ of the scattering point.

In an embodiment of the present disclosure, calculating a curvature of each point on the first defect profile curve in the planar polar coordinate system by solving a first derivative and a second derivative of a function of the first defect profile curve includes:

calculating a curvature $C_j(\theta_j, r_j)$ for any point $P_{Cj}(\theta_j, r_j)$ on the first defect profile curve by a formula:

$$C_j(\theta_j, r_j) = \frac{\left| r_j^2 + 2*\left(\frac{dr}{d\theta}\Big|\theta_j\right)^2 - r_j*\left(\frac{d^2r}{d\theta^2}\Big|\theta_j\right) \right|}{\left[ r_j^2 + \left(\frac{dr}{d\theta}\Big|\theta_j\right)^2 \right]^{\frac{3}{2}}}.$$

In an embodiment of the present disclosure, determining an array adjustment region by comparing the curvature of the each point with a preset curvature threshold, and adjusting the array structure according to the array adjustment region includes:

solving the array adjustment region $R(\theta)$ by a formula:

$R(\theta) = \arg \{\theta_j\} s.t. \ C_j(\theta_j) > C_{TH}$, where $C_{TH}$ is the preset curvature threshold; and according to the array adjustment region $R(\theta)$, canceling the electromagnetic acoustic transducer arranged in a portion of the initial array structure outside the array adjustment region $R(\theta)$; and for the array adjustment region $R(\theta)$, increasing a number density of the electromagnetic acoustic transducers therein and reducing a gap between adjacent electromagnetic acoustic transducers therein.

In an embodiment of the present disclosure, performing data fusion on the first defect profile curve and the second defect profile curve so as to form a defect profile image of the metal plate to be detected includes:

performing data fusion on the first defect profile curve determined before the array structure adjustment and the second defect profile curve determined after the array structure adjustment by a formula:

$PC_F(\theta_m, r_m) = \{P_{Ck}(\theta_k, r_k) \ s.t. \ \theta_m \in R(\theta)\} \cup \{P_{Cj}(\theta_j, r_j) \ s.t. \ \theta_m \notin R(\theta)\}$, where $PC_F(\theta_m, r_m)$ represents a third defect profile curve obtained after the data fusion and also represents a set of points thereon, m=1, 2, . . . M, M is a positive integer and represents a total number of the points on the third defect profile curve, $P_{Ck}(\theta_k, r_k)$ represents a point on the second defect profile curve, k=1, 2, . . . , K, and K is a positive integer and indicates a total number of points on the second defect profile curve, and in the planar polar coordinate system, the second defect profile curve and the function thereof is $PC(\theta_k, r_k)$.

With the method for adjusting an array structure of omnidirectional electromagnetic acoustic transducers for imaging a defect profile of a metal plate according to an embodiment of the present disclosure, a guided wave is excited and received by omnidirectional electromagnetic acoustic transducers, a position of a scattering point is solved using a travel time and a signal intensity of a guided wave signal and a first defect profile curve is established, an array adjustment region is solved by calculating a curvature of each point on the first defect profile curve, the array structure is adjusted and optimized, a second defect profile curve is calculated, and data fusion is performed on the first defect profile curve and the second defect profile curve so as to form a high-precision image of the complex defect profile. In the method, calculations are rapid, accurate and efficient. Moreover, with the method, the array structure can be adjusted and optimized for defects with different profile types, so that the defect profile imaging process is more targeted, thereby solving the serious mismatch problem between the transducer array having a particular regular structure and actual complex defects with varied scattering characteristics, and improving the imaging precision of the complex defect profiles.

According to an embodiment of a second aspect of the present disclosure, a device for adjusting an array structure of omnidirectional electromagnetic acoustic transducers for imaging a defect profile of a metal plate is provided, the device includes:

a processor; and a memory for storing instructions executable by the processor;

in which the processor is configured to perform the method for adjusting an array structure of omnidirectional electromagnetic acoustic transducers for imaging a defect profile of a metal plate as described in the above embodiments.

According to an embodiment of a third aspect of the present disclosure, there is provided a non-transitory computer-readable storage medium having stored therein instructions that, when executed by a processor of a mobile terminal, causes the mobile terminal to perform the method for adjusting an array structure of omnidirectional electromagnetic acoustic transducers for imaging a defect profile of a metal plate as described in the above embodiments.

Additional aspects and advantages of embodiments of the present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference to the drawings as described below.

DETAILED DESCRIPTION

Figure 1:
FIG. 1 is a flow chart of a method for adjusting an array structure of omnidirectional electromagnetic acoustic transducers for imaging a defect profile of a metal plate according to an embodiment of the present disclosure.

Reference will be made in detail to embodiments of the present disclosure. The embodiments described herein with reference to drawings are explanatory, illustrative, and used to generally understand the present disclosure. The embodiments shall not be construed to limit the present disclosure. The same or similar elements and the elements having same or similar functions are denoted by like reference numerals throughout the descriptions.

A method and a device for adjusting an array structure of omnidirectional electromagnetic acoustic transducers for imaging a defect profile of a metal plate according to embodiments of the present disclosure will be described below with reference to the accompanying drawings.

At present, requirements on the safety of the metal plate are increasingly strict, and thus defect detection is developing towards profile description, high-precision imaging, and visualization of detection results.

In the related art, an ultrasonic guided wave has the following features: low attenuation, far propagation distance, 100% coverage of the thickness of the metal plate by a sound field, easy adjustment of a guided wave mode, etc. Moreover, detection with guided waves of omnidirectional electromagnetic acoustic transducers for an area surrounded by the transducer array from multiple angles can provide more abundant and accurate defect information for high-precision imaging of the defect.

However, a transducer array in a specific geometric structure only has a best matching-degree and sensitivity to a defect having the specific scattering feature. In fact, an actual defect is very complex, and shape and scattering characteristics thereof are varied, therefore, a serious mismatch is present between the transducer array in the specific geometric structure and the actual complex defect with varied scattering characteristics, and the transducer array in the specific geometric structure cannot always maintain a high sensitivity to the actual complex defect, thereby resulting in a limited detection and imaging precision to the actual defect.

In order to address the above-mentioned problems, a method for adjusting an array structure of omnidirectional electromagnetic acoustic transducers for imaging a defect profile of a metal plate is provided in embodiments of the present disclosure, with the method, the array structure can be adjusted and optimized for defects with different profile types, so that the defect profile imaging process is more targeted, thereby solving the serious mismatch problem between the transducer array having a particular regular structure and actual complex defects with varied scattering characteristics, and improving the imaging precision of the complex defect profiles. Moreover, in the method, calculations are rapid, accurate and efficient. Details are as follows.

FIG. 1 is a flow chart of a method for adjusting an array structure of omnidirectional electromagnetic acoustic transducers for imaging a defect profile of a metal plate according to an embodiment of the present disclosure.

As shown in FIG. 1, the method for adjusting an array structure of omnidirectional electromagnetic acoustic transducers for imaging a defect profile of a metal plate includes the following blocks.

Block 11: N omnidirectional electromagnetic acoustic transducers are uniformly arranged in a detection region of the metal plate to be detected, in which each of the omnidirectional electromagnetic acoustic transducers is used as an omnidirectionally emitting electromagnetic acoustic transducer to excite an omnidirectional ultrasonic guided wave in a certain order, and used as an omnidirectionally receiving electromagnetic acoustic transducer to omnidirectionally receive a guided wave scattering signal of the defect when an ultrasonic guided wave is present in the detection region of the metal plate to be detected.

Specifically, the N omnidirectional electromagnetic acoustic transducers may be arranged in any form as long as they are uniformly arranged in the detection region of the metal plate to be detected. For example, the N omnidirectional electromagnetic acoustic transducers are uniformly arranged in a circular array.

It may be appreciated that each of the omnidirectional electromagnetic acoustic transducers excites an omnidirectional ultrasonic guided wave in a certain order in the detection region of the metal plate to be detected, and thus the omnidirectional ultrasonic guided wave may be excited form an $n^{th}$ omnidirectional electromagnetic acoustic transducer as the omnidirectionally emitting electromagnetic acoustic transducer. It may also be appreciated that each of the omnidirectional electromagnetic acoustic transducers is used as the omnidirectionally receiving electromagnetic acoustic transducer to omnidirectionally receive a guided wave scattering signal of a defect when there is an ultrasonic guided wave in the detection region of the metal plate to be detected. That is, each of the omnidirectional electromagnetic acoustic transducers has dual functions of exciting the omnidirectional ultrasonic guided wave and omnidirectionally receiving the guided wave scattering signal of the defect.

As a possible implementation, there are 3 omnidirectional electromagnetic acoustic transducers A, B and C, firstly, A as an excitation electromagnetic acoustic transducer excites the omnidirectional ultrasonic guided wave, and B and C as omnidirectionally receiving electromagnetic acoustic transducers omnidirectionally receive the guided wave scattering signal of the defect; then, B as the excitation electromagnetic acoustic transducer excites the omnidirectional ultrasonic guided wave, and A and C as omnidirectionally receiving electromagnetic acoustic transducers omnidirectionally receive the guided wave scattering signal of the defect; finally, C as the excitation electromagnetic acoustic transducer excites the omnidirectional ultrasonic guided wave, and A and B as omnidirectionally receiving electromagnetic acoustic transducers omnidirectionally receive the guided wave scattering signal of the defect.

It should be noted that the omnidirectional ultrasonic guided wave is excited in an order of ABC as mentioned above, which is just used to illustrate the present disclosure, and shall not be construed to limit the present disclosure. The omnidirectional ultrasonic guided wave may also be excited in other orders, such as in an order of BAC or CAB.

It should be noted that the omnidirectional electromagnetic acoustic transducer mainly consists of a cake-shaped densely packed circumferential coil powered by an alternating current, an open-ended nickel ribbon ring top-magnetized in a circumferential direction, and the metal plate to be detected itself below the omnidirectional electromagnetic acoustic transducer.

For example, 16 omnidirectional electromagnetic acoustic transducers (i.e., omnidirectionally emitting/receiving EMATs) are uniformly arranged around a detection region of a steel plate to be detected in a circular array. The thickness of the steel plate is 4 mm, the diameter of the omnidirectionally emitting/receiving EMATs is 35 mm, and the diameter of the circular array is 54 cm.

Block 12: a position of a scattering point is calculated according to an amplitude and travel time of the guided wave scattering signal of the defect, and a first defect profile curve is formed by performing three smooth spline interpolations on coordinate data of the position of the scattering point.

Specifically, a planar polar coordinate system is established, and the position of the scattering point is calculated by formula (1) and formula (2):

$$|\vec{TP}| + |\vec{PR}| = v * t_r \quad (1)$$

$$A * \frac{1}{\sqrt{|\vec{TP}|}} * a_s * \frac{1}{\sqrt{|\vec{PR}|}} = A_{RS}, \quad (2)$$

where $t_r$ is an actually measured travel time of the guided wave scattering signal of the defect, v is a propagation velocity of the guided wave scattering signal of the defect in the metal plate, T is a position of the omnidirectionally emitting electromagnetic acoustic transducer, R is a position of the omnidirectionally receiving electromagnetic acoustic transducer, A is a signal intensity of the omnidirectional ultrasonic guided wave excited at the position T of the omnidirectionally emitting electromagnetic acoustic transducer, $a_s$ is a scattering attenuation coefficient of the signal intensity when the ultrasonic guided wave is scattered, and $A_{RS}$ is an intensity of the guided wave scattering signal of the defect received at the position R of the omnidirectionally receiving electromagnetic acoustic transducer.

Specifically, three smooth spline interpolations are performed on polar coordinates $P_i(\theta_i, r_i)$ of S scattering points obtained to form the first defect profile curve and a function $PC(\theta_j, r_j)$ thereof, where S is a positive integer, and $P_i(\theta_i, r_i)$ is the polar coordinate of the scattering point, where i=1, 2, . . . , S, $$PC(\theta_j, r_j) = CSplineI[P_i(\theta_i, r_i)],$$

where j=1, 2, . . . , S1, and S1 is a positive integer and represents a total number of the points on the first defect profile curve, CSplineI is a function for performing three smooth spline interpolations on the polar coordinate $P_i(\theta_i, r_i)$ of the scattering point.

Block 13: a curvature of each point on the first defect profile curve is calculated by solving a first derivative and a second derivative of a function of the first defect profile curve in the planar polar coordinate system.

Specifically, the curvature of each point on the defect profile curve may be acquired in many ways, e.g., a preset algorithm, a preset formula, etc., which can be selected or set according to the actual application requirements. In this embodiment, the curvature $C_j(\theta_j, r_j)$ for any point $P_{Cj}(\theta_j, r_j)$ on the first defect profile curve may be calculated by formula (3):

$$C_j(\theta_j, r_j) = \frac{\left| r_j^2 + 2*\left(\frac{dr}{d\theta}\Big|\theta_j\right)^2 - r_j*\left(\frac{d^2r}{d\theta^2}\Big|\theta_j\right) \right|}{\left[r_j^2 + \left(\frac{dr}{d\theta}\Big|\theta_j\right)^2\right]^{\frac{3}{2}}}. \quad (3)$$

Block 14: an array adjustment region is determined by comparing the curvature of the each point with a preset curvature threshold, the array structure is adjusted according to the array adjustment region, and a second defect profile curve of the guided wave scattering signal of the defect is calculated.

Specifically, the curvature threshold is preset, and the value thereof may be selected or set depending on the actual application needs. It may be appreciated that it is determined whether a curvature of a point on the first defect profile curve exceeds the preset curvature threshold, if yes, the point enters into the adjustment region; and if no, it is determined whether curvatures of all points on the first defect profile curve are calculated and compared with the preset curvature threshold, if yes, entering the adjustment region; if no, turning to the next point on the first defect profile curve, turning to $P_{Cj+1}(\theta_{j+1}, r_{j+1})$.

Specifically, the array adjustment region $R(\theta)$ is solved by a formula:

$$R(\theta) = \arg\{\theta_j\} s.t.\ C_j(\theta_j) > C_{TH},$$

where $C_{TH}$ is the preset curvature threshold.

Figure 2:
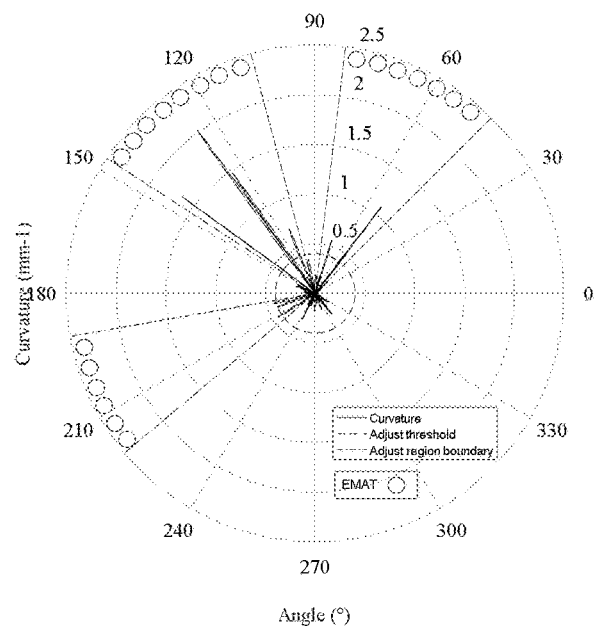
FIG. 2 is a schematic diagram showing an array structure adjustment according to an embodiment of the present disclosure.

Specifically, according to the array adjustment region $R(\theta)$, the electromagnetic acoustic transducer arranged in a portion of the initial array structure outside the array adjustment region $R(\theta)$ is canceled; and for the array adjustment region $R(\theta)$, a number density of the electromagnetic acoustic transducers therein is increased and a gap between adjacent electromagnetic acoustic transducers therein is reduced. That is, the electromagnetic acoustic transducers are mainly concentrated within the array adjustment region. FIG. 2 is a schematic diagram showing an array structure adjustment according to an embodiment of the present disclosure. As shown in FIG. 2, it can be seen that the array structure after adjustment is not uniform any more.

Block 15: data fusion is performed on the first defect profile curve and the second defect profile curve so as to form a defect profile image of the metal plate to be detected.

Specifically, data fusion is performed on the first defect profile curve determined before the array structure adjustment and the second defect profile curve determined after the array structure adjustment by a formula (4):

$$PC_F(\theta_m, r_m) = \{P_{Ck}(\theta_k, r_k)\ s.t.\ \theta_m \in R(\theta)\} \cup \{P_{Cj}(\theta_j, r_j)\ s.t.\ \theta_m \notin R(\theta)\} \quad (4),$$

where $PC_F(\theta_m, r_m)$ represents a third defect profile curve obtained after the data fusion and also represents a set of points thereon, m=1, 2, . . . M, and M is a positive integer and represents a total number of the points on the third defect profile curve, $P_{Ck}(\theta_k, r_k)$ represents a point on the second defect profile curve, in the planar polar coordinate system, the second defect profile curve and the function thereof is $PC(\theta_k, r_k)$, k=1, 2, . . . , K, and K is a positive integer and indicates a total number of points on the second defect profile curve.

Figure 3:
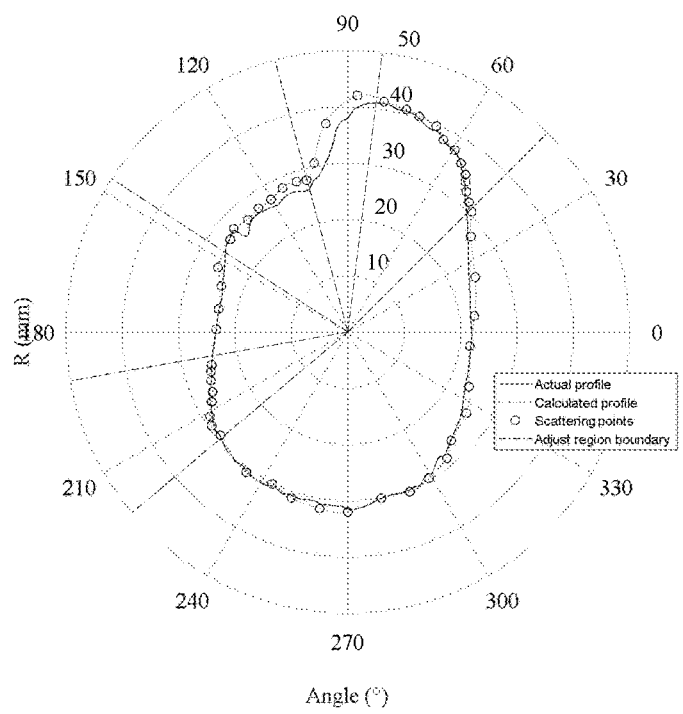
FIG. 3 is a diagram showing a defect profile imaging result of a metal plate according to an embodiment of the present disclosure.

FIG. 3 is a diagram showing a defect profile imaging result of a metal plate according to an embodiment of the present disclosure. As shown in FIG. 3, the defect profile curve after data fusion has been very close to the actual defect profile of this steel plate. With the method of the present disclosure, the array structure is adjusted for the defects with different profile types, and thus the detection is more targeted with high efficiency, and a clear profile image of the defect can be obtained.

In summary, with the method for adjusting an array structure of omnidirectional electromagnetic acoustic transducers for imaging a defect profile of a metal plate according to an embodiment of the present disclosure, a guided wave is excited and received by omnidirectional electromagnetic acoustic transducers, a position of a scattering point is solved using a travel time and a signal intensity of a guided wave signal and a first defect profile curve is established, an array adjustment region is solved by calculating a curvature of each point on the first defect profile curve, the array structure is adjusted and optimized, a second defect profile curve is calculated, and data fusion is performed on the first defect profile curve and the second defect profile curve so as to form a high-precision image of the complex defect profile. In the method, calculations are rapid, accurate and efficient. Moreover, with the method, the array structure can be adjusted and optimized for defects with different profile types, so that the defect profile imaging process is more targeted, thereby solving the serious mismatch problem between the transducer array having a particular regular structure and actual complex defects with varied scattering characteristics, and improving the imaging precision of the complex defect profiles.

Figure 4:
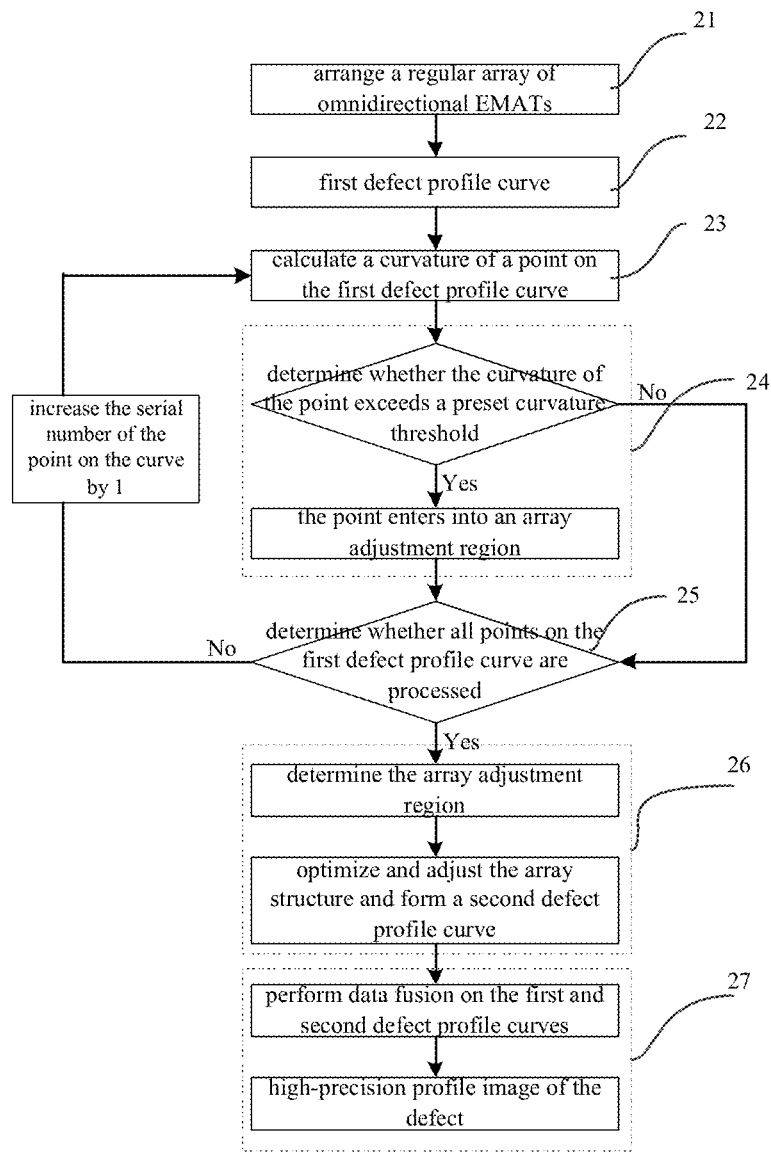
FIG. 4 is a flow chart of a method for adjusting an array structure of omnidirectional electromagnetic acoustic transducers for imaging a defect profile of a metal plate according to another embodiment of the present disclosure.

FIG. 4 is a flow chart of a method for adjusting an array structure of omnidirectional electromagnetic acoustic transducers for imaging a defect profile of a metal plate according to another embodiment of the present disclosure. In order to make those skilled in the art to understand the present disclosure more clearly, in the following, the method for adjusting an array structure of omnidirectional electromagnetic acoustic transducers for imaging a defect profile of a metal plate will be described with reference to FIG. 4.

As shown in FIG. 4, the method for adjusting an array structure of omnidirectional electromagnetic acoustic transducers for imaging a defect profile of a metal plate includes the following blocks.

Block 21: 12 omnidirectional electromagnetic acoustic transducers (i.e., omnidirectionally emitting/receiving EMATs) are uniformly arranged within a detection region of a steel plate to be detected in a circular array. The thickness of the steel plate is 3 mm, the diameter of the omnidirectionally emitting/receiving EMATs is 35 mm, and the diameter of the circular array is 46 cm.

Block 22: a position P of a scattering point is solved according to an amplitude and travel time of a guided wave scattering signal of a defect received by the omnidirectionally receiving EMAT. For a certain ultrasonic guided wave detection signal received by the omnidirectionally receiving EMAT, an actually measured travel time thereof is $t_r$, a propagation velocity of the ultrasonic guided wave in the metal plate is v (3200 m/s). A planar polar coordinate system is established, a position of the omnidirectional emitting EMAT is T, a position of the omnidirectionally receiving EMAT is R, and the position of the scattering point is calculated by formula (1) and formula (2):

$$|\vec{TP}| + |\vec{PR}| = v * t_r \quad (1)$$

$$A * \frac{1}{\sqrt{|\vec{TP}|}} * a_s * \frac{1}{\sqrt{|\vec{PR}|}} = A_{RS}, \quad (2)$$

where A is a signal intensity of the omnidirectional ultrasonic guided wave excited at the position T of the omnidirectionally emitting EMAT, $a_s$ is a scattering attenuation coefficient of the signal intensity when the ultrasonic guided wave is scattered, and $A_{RS}$ is a signal intensity of a scattered wave received at the position R of the omnidirectionally receiving EMAT.

A first defect profile curve is formed by performing three smooth spline interpolations on coordinate data of the position of the scattering point.

S scattering points are obtained in total, where S is a positive integer, for example, S is 27 in this embodiment, the polar coordinates thereof are $P_i(\theta_i, r_i)$, where i=1, 2, ..., S, and the first defect profile curve and a function $PC(\theta_j, r_j)$ thereof is formed by performing three smooth spline interpolations on polar coordinates of the scattering points:

$$PC(\theta_j, r_j) = CSplineI[P_i(\theta_i, r_i)],$$

where j=1, 2, ..., S1, and S1 is a positive integer and represents a total number of the points on the first defect profile curve, for example, S1 is 1600 in this embodiment, CSplineI is a function for performing three smooth spline interpolations for the polar coordinates $P_i(\theta_i, r_i)$ of the scattering points.

Block 23: a curvature $C_j(\theta_j, r_j)$ of a point $P_{Cj}(\theta_j, r_j)$ on the first defect profile curve is calculated by solving a first derivative and a second derivative of the function $PC(\theta_j, r_j)$ of the first defect profile curve at the point according to formula (3):

$$C_j(\theta_j, r_j) = \frac{\left| r_j^2 + 2 * \left(\frac{dr}{d\theta}\bigg|\theta_j\right)^2 - r_j * \left(\frac{d^2r}{d\theta^2}\bigg|\theta_j\right) \right|}{\left[ r_j^2 + \left(\frac{dr}{d\theta}\bigg|\theta_j\right)^2 \right]^{\frac{3}{2}}}. \quad (3)$$

Block 24: it is determined whether the curvature of the point on the first defect profile curve calculated in Block 23 exceeds the curvature threshold, if yes, the point enters into the adjustment region; if no, Block 25 is performed.

Block 25: it is determined whether the curvatures of all points on the first defect profile curve has already been calculated and compared with the preset curvature threshold, if yes, performing Block 26; if no, turning to a point $P_{Cj+1}(\theta_{j+1}, r_{j+1})$ on the first defect profile curve, and returning to Block 23.

Block 26: in the planar polar coordinate system, an array adjustment region R(θ) is determined, the array structure is optimized and adjusted, and a second defect profile curve is calculated.

In the planar polar coordinate system, the array adjustment region R(θ) is solved by a formula:

$$R(\theta) = \arg \{\theta_j\} s.t. \ C_j(\theta_j) > C_{TH},$$

where $C_{TH}$ is the preset curvature threshold and may be 1.2 in this embodiment.

The method for optimizing and adjusting the array structure includes: according to the solved array adjustment region R(θ), canceling the electromagnetic acoustic transducer arranged in a portion of the initial array structure outside the array adjustment region R(θ); and for the array adjustment region R(θ), increasing a number density of the electromagnetic acoustic transducers therein and reducing a gap between adjacent electromagnetic acoustic transducers therein, that is, the electromagnetic acoustic transducers are mainly concentrated within the array adjustment region.

Block 27: data fusion is performed on the first defect profile curve determined before the array structure adjustment and the second defect profile curve determined after the array structure adjustment. In the planar polar coordinate system, the second defect profile curve and the function thereof calculated after the array structure adjustment is $PC(\theta_k, r_k)$, and a point on the second defect profile curve is expressed as $P_{Ck}(\theta_k, r_k)$, where k=1, 2, ..., K, K is a positive integer and indicates a total number of points on the second defect profile curve calculated after the array structure adjustment (the total number of points is 1000 in this embodiment). A formula for performing the data fusion on the first defect profile curve determined before the array structure adjustment and the second defect profile curve determined after the array structure adjustment is formula (4):

$$PC_F(\theta_m, r_m) = \{P_{Ck}(\theta_k, r_k) \text{ s.t. } \theta_m \in R(\theta)\} \cup \{P_{Cj}(\theta_j, r_j) \text{ s.t. } \theta_m \notin R(\theta)\} \quad (4),$$

where $PC_F(\theta_m, r_m)$ represents a third defect profile curve obtained after the data fusion and also represents a set of points thereon, m=1, 2, ... M, and M is a positive integer and represents a total number of points on the third defect profile curve.

In addition, other configurations and functions thereof in the method for adjusting an array structure of omnidirectional electromagnetic acoustic transducers for imaging a defect profile of a metal plate according to an embodiment of the present disclosure are known to those skilled in the art, which will not be elaborated herein.

In summary, with the method for adjusting an array structure of omnidirectional electromagnetic acoustic transducers for imaging a defect profile of a metal plate according to an embodiment of the present disclosure, a guided wave is excited and received by omnidirectional electromagnetic acoustic transducers, a position of a scattering point is solved using a travel time and a signal intensity of a guided wave signal and a first defect profile curve is established, an array adjustment region is solved by calculating a curvature of each point on the first defect profile curve, the array structure is adjusted and optimized, a second defect profile curve is calculated, and data fusion is performed on the first defect profile curve and the second defect profile curve so as to form a high-precision image of the complex defect profile. In the method, calculations are rapid, accurate and efficient. Moreover, with the method, the array structure can be adjusted and optimized for defects with different profile types, so that the defect profile imaging process is more targeted, thereby solving the serious mismatch problem between the transducer array having a particular regular structure and actual complex defects with varied scattering characteristics, and improving the imaging precision of the complex defect profiles.

In order to achieve the above-described embodiments, an apparatus for adjusting an array structure of omnidirectional electromagnetic acoustic transducers for imaging a defect profile of a metal plate is also provided in the present disclosure.

Figure 5:
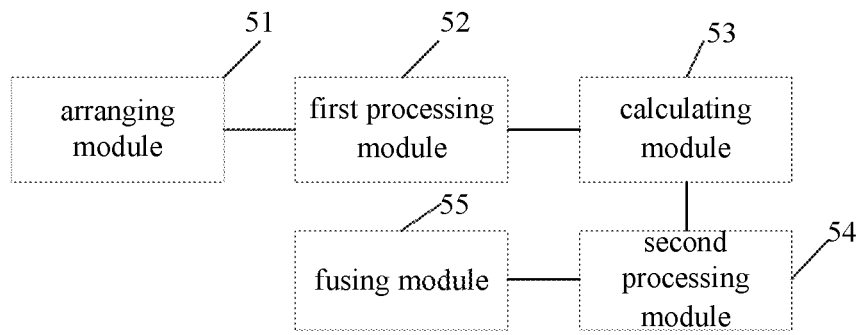
FIG. 5 is a schematic block diagram of an apparatus for adjusting an array structure of omnidirectional electromagnetic acoustic transducers for imaging a defect profile of a metal plate according to an embodiment of the present disclosure.

FIG. 5 is a schematic block diagram of an apparatus for adjusting an array structure of omnidirectional electromagnetic acoustic transducers for imaging a defect profile of a metal plate according to an embodiment of the present disclosure.

As shown in FIG. 5, the apparatus for adjusting an array structure of omnidirectional electromagnetic acoustic transducers for imaging a defect profile of a metal plate includes an arranging module 51, a first processing module 52, a calculating module 53, a second processing module 54, and a fusing module 55.

The arranging module 51 is configured to uniformly arrange N omnidirectional electromagnetic acoustic transducers in a detection region of a metal plate to be detected, in which each of the omnidirectional electromagnetic acoustic transducers is used as an omnidirectionally emitting electromagnetic acoustic transducer to excite an omnidirectional ultrasonic guided wave in a certain order, and used as an omnidirectionally receiving electromagnetic acoustic transducer to omnidirectionally receive a guided wave scattering signal of a defect when an ultrasonic guided wave is present in the detection region of the metal plate to be detected.

The first processing module 52 is configured to calculate a position of a scattering point according to an amplitude and travel time of the guided wave scattering signal of the defect, and configured to form a first defect profile curve by performing three smooth spline interpolations on coordinate data of the position of the scattering point.

The calculating module 53 is configured to calculate a curvature of each point on the first defect profile curve in a planar polar coordinate system by solving a first derivative and a second derivative of a function of the first defect profile curve.

The second processing module 54 is configured to determine an array adjustment region by comparing the curvature of the each point with a preset curvature threshold, to adjust the array structure according to the array adjustment region, and to calculate a second defect profile curve of the guided wave scattering signal of the defect.

The fusing module 55 is configured to perform data fusion on the first defect profile curve and the second defect profile curve so as to form a defect profile image of the metal plate to be detected.

In an embodiment of the present disclosure, the first processing module 52 is configured to: establish the planar polar coordinate system, and calculate the position of the scattering point by following formulas:

$$|\overrightarrow{TP}| + |\overrightarrow{PR}| = v * t_r$$

$$A * \frac{1}{\sqrt{|\overrightarrow{TP}|}} * a_s * \frac{1}{\sqrt{|\overrightarrow{PR}|}} = A_{RS},$$

where $t_r$ is an actually measured travel time of the guided wave scattering signal of the defect, v is a propagation velocity of the guided wave scattering signal of the defect in the metal plate, T is a position of the omnidirectionally emitting electromagnetic acoustic transducer, R is a position of the omnidirectionally receiving electromagnetic acoustic transducer, A is a signal intensity of the omnidirectional ultrasonic guided wave excited at the position T of the omnidirectionally emitting electromagnetic acoustic transducer, $a_s$ is a scattering attenuation coefficient of the signal intensity when the ultrasonic guided wave is scattered, and $A_{RS}$ is an intensity of the guided wave scattering signal of the defect received at the position R of the omnidirectionally receiving electromagnetic acoustic transducer; and the first processing module 52 is further configured to: perform three smooth spline interpolations on polar coordinates $P_i(\theta_i, r_i)$ of S scattering points obtained to form the first defect profile curve and the function $PC(\theta_j, r_j)$ thereof, where S is a positive integer, and $P_i(\theta_i, r_i)$ is the polar coordinate of the scattering point, where i=1, 2, ..., S, $$PC(\theta_j, r_j)=CSplineI[P_i(\theta_i, r_i)],$$

where j=1, 2, ..., S1, and S1 is a positive integer and represents a total number of the points on the first defect profile curve, CSplineI is a function for performing three smooth spline interpolations on the polar coordinate $P_i(\theta_i, r_i)$ of the scattering point.

In an embodiment of the present disclosure, the calculating module 53 is configured to calculate a curvature $C_j(\theta_j, r_j)$ for any point $P_{Cj}(\theta_j, r_j)$ on the first defect profile curve by a formula:

$$C_j(\theta_j, r_j) = \frac{\left|r_j^2 + 2*\left(\frac{dr}{d\theta}\Big|\theta_j\right)^2 - r_j*\left(\frac{d^2r}{d\theta^2}|\theta_j\right)\right|}{\left[r_j^2 + \left(\frac{dr}{d\theta}\Big|\theta_j\right)^2\right]^{\frac{3}{2}}}.$$

In an embodiment of the present disclosure, the second processing module 54 is configured to solve the array adjustment region $R(\theta)$ by a formula: $R(\theta)=\arg\{\theta_j\}$ s.t. $C_j(\theta_j)>C_{TH}$, where $C_{TH}$ is the preset curvature threshold; and to cancel, according to the array adjustment region $R(\theta)$, the electromagnetic acoustic transducer arranged in a portion of the initial array structure outside the array adjustment region $R(\theta)$; and for the array adjustment region $R(\theta)$, to increase a number density of the electromagnetic acoustic transducers therein and to reduce a gap between adjacent electromagnetic acoustic transducers therein.

In an embodiment of the present disclosure, the fusing module 55 is configured to: perform data fusion on the first defect profile curve determined before the array structure adjustment and the second defect profile curve determined after the array structure adjustment by a formula:

$$PC_F(\theta_m, r_m)=\{P_{Ck}(\theta_k, r_k) \text{ s.t. } \theta_m \in R(\theta)\} \cup \{P_{Cj}(\theta_j, r_j) \text{ s.t. } \theta_m \notin R(\theta)\},$$

where $PC_F(\theta_m, r_m)$ represents a third defect profile curve obtained after the data fusion and also represents a set of points thereon, m=1, 2, ... M, M is a positive integer and represents a total number of the points on the third defect profile curve, $P_{Ck}(\theta_k, r_k)$ represents a point on the second defect profile curve, k=1, 2, ..., K, and K is a positive integer and indicates a total number of points on the second defect profile curve, and in the planar polar coordinate system, the second defect profile curve and the function thereof is $PC(\theta_k, r_k)$.

It should be noted that the foregoing explanations for the method for adjusting an array structure of omnidirectional electromagnetic acoustic transducers for imaging a defect profile of a metal plate according to the embodiments of the present disclosure is also applicable to the device for adjusting an array structure of omnidirectional electromagnetic acoustic transducers for imaging a defect profile of a metal plate according to the embodiments of the present disclosure, which will not be elaborated herein.

In summary, with the apparatus for adjusting an array structure of omnidirectional electromagnetic acoustic transducers for imaging a defect profile of a metal plate according to an embodiment of the present disclosure, a guided wave is excited and received by omnidirectional electromagnetic acoustic transducers, a position of a scattering point is solved using a travel time and a signal intensity of a guided wave signal and a first defect profile curve is established, an array adjustment region is solved by calculating a curvature of each point on the first defect profile curve, the array structure is adjusted and optimized, a second defect profile curve is calculated, and data fusion is performed on the first defect profile curve and the second defect profile curve so as to form a high-precision image of the complex defect profile. With the apparatus, calculations are rapid, accurate and efficient, and the array structure can be adjusted and optimized for defects with different profile types, so that the defect profile imaging process is more targeted, thereby solving the serious mismatch problem between the transducer array having a particular regular structure and actual complex defects with varied scattering characteristics, and improving the imaging precision of the complex defect profiles.

In embodiments of the present disclosure, a device for adjusting an array structure of omnidirectional electromagnetic acoustic transducers for imaging a defect profile of a metal plate is also provided, the device includes: a processor; and a memory for storing instructions executable by the processor, in which the processor is configured to perform the method for adjusting an array structure of omnidirectional electromagnetic acoustic transducers for imaging a defect profile of a metal plate as described in the above embodiments.

In embodiments of the present disclosure, there is also provided a non-transitory computer-readable storage medium having stored therein instructions that, when executed by a processor of a mobile terminal, causes the mobile terminal to perform the method for adjusting an array structure of omnidirectional electromagnetic acoustic transducers for imaging a defect profile of a metal plate as described in the above embodiments.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "In an embodiment," in various places throughout this specification are not necessarily referring to the same embodiment or example of the present disclosure. Furthermore, the particular features, structures, materials, or characteristics may be combined in any suitable manner in one or more embodiments or examples.

In addition, terms such as "first" and "second" are used herein for purposes of description and are not intended to indicate or imply relative importance or significance. Thus, the feature defined with "first" and "second" may include one or more this feature. In the description of the present disclosure, a phrase of "a plurality of" means two or more than two, unless specified otherwise.

It will be understood that, any process or method described in a flow chart or described herein in other ways may be understood to include one or more modules, segments or portions of codes of executable instructions for achieving specific logical functions or steps in the process, and the scope of a preferred embodiment of the present disclosure includes other implementations, in which the order of execution is different from what is shown or discussed, including executing functions in a substantially simultaneous manner or in an opposite order according to the related functions. These and other aspects should be understood by those skilled in the art.

It can be understood that all or part of the steps in the method of the above embodiments can be implemented by instructing related hardware via programs, the program may be stored in a computer readable storage medium, and the program includes one step or combinations of the steps of the method when the program is executed.

In addition, each functional unit in the present disclosure may be integrated in one processing module, or each functional unit exists as an independent unit, or two or more functional units may be integrated in one module. The integrated module can be embodied in hardware, or software. If the integrated module is embodied in software and sold or used as an independent product, it can be stored in the computer readable storage medium.

The above mentioned storage medium may be read-only memories, magnetic disks, or optical disks. Although explanatory embodiments of the present disclosure have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A method for adjusting an array structure of omnidirectional electromagnetic acoustic transducers for imaging a defect profile of a metal plate, comprising:
    uniformly arranging N omnidirectional electromagnetic acoustic transducers in a detection region of the metal plate to be detected, wherein each of the omnidirectional electromagnetic acoustic transducers is used as an omnidirectionally emitting electromagnetic acoustic transducer to excite an omnidirectional ultrasonic guided wave in a certain order, and used as an omnidirectionally receiving electromagnetic acoustic transducer to omnidirectionally receive a guided wave scattering signal of a defect when an ultrasonic guided wave is present in the detection region of the metal plate to be detected;
    calculating a position of a scattering point according to an amplitude and travel time of the guided wave scattering signal of the defect, and forming a first defect profile curve by performing three smooth spline interpolations on coordinate data of the position of the scattering point;
    calculating a curvature of each point on the first defect profile curve in a planar polar coordinate system by solving a first derivative and a second derivative of a function of the first defect profile curve;
    determining an array adjustment region by comparing the curvature of the each point with a preset curvature threshold, adjusting the array structure according to the array adjustment region, and calculating a second defect profile curve of the guided wave scattering signal of the defect; and
    performing data fusion on the first defect profile curve and the second defect profile curve so as to form a defect profile image of the metal plate to be detected.

2. The method according to claim 1, wherein calculating a position of a scattering point according to an amplitude and travel time of the guided wave scattering signal of the defect, and forming a first defect profile curve by performing three smooth spline interpolations on coordinate data of the position of the scattering point comprises:
    establishing the planar polar coordinate system, and calculating the position of the scattering point by following formulas:

$$|\vec{TP}| + |\vec{PR}| = v * t_r$$

$$A * \frac{1}{\sqrt{|\vec{TP}|}} * a_s * \frac{1}{\sqrt{|\vec{PR}|}} = A_{RS},$$

where $t_r$ is an actually measured travel time of the guided wave scattering signal of the defect, v is a propagation velocity of the guided wave scattering signal of the defect in the metal plate, T is a position of the omnidirectionally emitting electromagnetic acoustic transducer, R is a position of the omnidirectionally receiving electromagnetic acoustic transducer, A is a signal intensity of the omnidirectional ultrasonic guided wave excited at the position T of the omnidirectionally emitting electromagnetic acoustic transducer, $a_s$ is a scattering attenuation coefficient of the signal intensity when the ultrasonic guided wave is scattered, and $A_{RS}$ is an intensity of the guided wave scattering signal of the defect received at the position R of the omnidirectionally receiving electromagnetic acoustic transducer; and performing three smooth spline interpolations on polar coordinates $P_i(\theta_i, r_i)$ of S scattering points obtained to form the first defect profile curve and the function $PC(\theta_j, r_j)$ thereof, where S is a positive integer, and $P_i(\theta_i, r_i)$ is the polar coordinate of the scattering point, where i=1, 2, . . . , S, $PC(\theta_j, r_j) = CSplineI[P_i(\theta_i, r_i)]$ where j=1, 2, . . . , S1, and S1 is a positive integer and represents a total number of the points on the first defect profile curve, CSplineI is a function for performing three smooth spline interpolations on the polar coordinate $P_i(\theta_i, r_i)$ of the scattering point.

3. The method according to claim 1, wherein calculating a curvature of each point on the first defect profile curve in the planar polar coordinate system by solving a first derivative and a second derivative of a function of the first defect profile curve comprises:
    calculating a curvature $C_j(\theta_j, r_j)$ for any point $P_{Cj}(\theta_j, r_j)$ on the first defect profile curve by a formula:

$$C_j(\theta_j, r_j) = \frac{\left| r_j^2 + 2 * \left(\frac{dr}{d\theta}\bigg|\theta_j\right)^2 - r_j * \left(\frac{d^2 r}{d\theta^2}\bigg|\theta_j\right) \right|}{\left[r_j^2 + \left(\frac{dr}{d\theta}\bigg|\theta_j\right)^2\right]^{\frac{3}{2}}}.$$

4. The method according to claim 1, wherein determining an array adjustment region by comparing the curvature of the each point with a preset curvature threshold, and adjusting the array structure according to the array adjustment region comprises:
    solving the array adjustment region $R(\theta)$ by a formula:

$R(\theta) = \arg \{\theta_j\} s.t. \; C_j(\theta_j) > C_{TH},$ where $C_{TH}$ is the preset curvature threshold; and
    according to the array adjustment region $R(\theta)$, canceling the electromagnetic acoustic transducer arranged in a portion of the initial array structure outside the array adjustment region R(θ); and for the array adjustment region R(θ), increasing a number density of the electromagnetic acoustic transducers therein and reducing a gap between adjacent electromagnetic acoustic transducers therein.

5. The method according to claim 1, wherein performing data fusion on the first defect profile curve and the second defect profile curve so as to form a defect profile image of the metal plate to be detected comprises:
performing data fusion on the first defect profile curve determined before the array structure adjustment and the second defect profile curve determined after the array structure adjustment by a formula:

$$PC_F(\theta_m, r_m) = \{P_{Ck}(\theta_k, r_k) \ s.t. \ \theta_m \in R(\theta)\} \cup \{P_{Cj}(\theta_j, r_j) \ s.t. \ \theta_m \notin R(\theta)\}$$

where $PC_F(\theta_m, r_m)$ represents a third defect profile curve obtained after the data fusion and also represents a set of points thereon, m=1, 2, ... M, M is a positive integer and represents a total number of the points on the third defect profile curve;
$P_{Ck}(\theta_k, r_k)$ represents a point on the second defect profile curve, k=1, 2, ..., K, and K is a positive integer and indicates a total number of points on the second defect profile curve;
wherein in the planar polar coordinate system, the second defect profile curve and the function thereof is $PC(\theta_k, r_k)$.

6. A device for adjusting an array structure of omnidirectional electromagnetic acoustic transducers for imaging a defect profile of a metal plate, comprising:
a processor; and
a memory for storing instructions executable by the processor;
wherein the processor is configured to perform a method for adjusting an array structure of omnidirectional electromagnetic acoustic transducers for imaging a defect profile of a metal plate, the method comprising:
uniformly arranging N omnidirectional electromagnetic acoustic transducers in a detection region of the metal plate to be detected, wherein each of the omnidirectional electromagnetic acoustic transducers is used as an omnidirectionally emitting electromagnetic acoustic transducer to excite an omnidirectional ultrasonic guided wave in a certain order, and used as an omnidirectionally receiving electromagnetic acoustic transducer to omnidirectionally receive a guided wave scattering signal of a defect when an ultrasonic guided wave is present in the detection region of the metal plate to be detected;
calculating a position of a scattering point according to an amplitude and travel time of the guided wave scattering signal of the defect, and forming a first defect profile curve by performing three smooth spline interpolations on coordinate data of the position of the scattering point;
calculating a curvature of each point on the first defect profile curve in a planar polar coordinate system by solving a first derivative and a second derivative of a function of the first defect profile curve;
determining an array adjustment region by comparing the curvature of the each point with a preset curvature threshold, adjusting the array structure according to the array adjustment region, and calculating a second defect profile curve of the guided wave scattering signal of the defect; and
performing data fusion on the first defect profile curve and the second defect profile curve so as to form a defect profile image of the metal plate to be detected.

7. The device according to claim 6, wherein calculating a position of a scattering point according to an amplitude and travel time of the guided wave scattering signal of the defect, and forming a first defect profile curve by performing three smooth spline interpolations on coordinate data of the position of the scattering point comprises:
establishing the planar polar coordinate system, and calculating the position of the scattering point by following formulas:

$$|\vec{TP}| + |\vec{PR}| = v * t_r$$

$$A * \frac{1}{\sqrt{|\vec{TP}|}} * a_s * \frac{1}{\sqrt{|\vec{PR}|}} = A_{RS},$$

where $t_r$ is an actually measured travel time of the guided wave scattering signal of the defect, v is a propagation velocity of the guided wave scattering signal of the defect in the metal plate, T is a position of the omnidirectionally emitting electromagnetic acoustic transducer, R is a position of the omnidirectionally receiving electromagnetic acoustic transducer, A is a signal intensity of the omnidirectional ultrasonic guided wave excited at the position T of the omnidirectionally emitting electromagnetic acoustic transducer, $a_s$ is a scattering attenuation coefficient of the signal intensity when the ultrasonic guided wave is scattered, and $A_{RS}$ is an intensity of the guided wave scattering signal of the defect received at the position R of the omnidirectionally receiving electromagnetic acoustic transducer; and
performing three smooth spline interpolations on polar coordinates $P_i(\theta_i, r_i)$ of S scattering points obtained to form the first defect profile curve and a function $PC(\theta_j, r_j)$ thereof, where S is a positive integer, and $P_i(\theta_i, r_i)$ is the polar coordinate of the scattering point, where i=1, 2, ..., S, $$PC(\theta_j, r_j) = CSplineI[P_i(\theta_i, r_i)]$$

where j=1, 2, ..., S1, and S1 is a positive integer and represents a total number of the points on the first defect profile curve, CSplineI is a function for performing three smooth spline interpolations on the polar coordinate $P_i(\theta_i, r_i)$ of the scattering point.

8. The device according to claim 6, wherein calculating a curvature of each point on the first defect profile curve in the planar polar coordinate system by solving a first derivative and a second derivative of a function of the first defect profile curve comprises:
calculating a curvature $C_j(\theta_j, r_j)$ for any point $P_{Cj}(\theta_j, r_j)$ on the first defect profile curve by a formula:

$$C_j(\theta_j, r_j) = \frac{\left| r_j^2 + 2 * \left(\frac{dr}{d\theta}\big|\theta_j\right)^2 - r_j * \left(\frac{d^2 r}{d\theta^2}\big|\theta_j\right) \right|}{\left[ r_j^2 + \left(\frac{dr}{d\theta}\big|\theta_j\right)^2 \right]^{\frac{3}{2}}}.$$

9. The device according to claim 6, wherein determining an array adjustment region by comparing the curvature of the each point with a preset curvature threshold, and adjusting the array structure according to the array adjustment region comprises:

solving the array adjustment region $R(\theta)$ by a formula:

$$R(\theta)=\arg\{\theta_j\} s.t.\ C_j(\theta_j)>C_{TH},$$

where $C_{TH}$ is the preset curvature threshold; and
according to the array adjustment region $R(\theta)$, canceling the electromagnetic acoustic transducer arranged in a portion of the initial array structure outside the array adjustment region $R(\theta)$; and for the array adjustment region $R(\theta)$, increasing a number density of the electromagnetic acoustic transducers therein and reducing a gap between adjacent electromagnetic acoustic transducers therein.

10. The device according to claim 6, wherein performing data fusion on the first defect profile curve and the second defect profile curve so as to form a defect profile image of the metal plate to be detected comprises:

performing data fusion on the first defect profile curve determined before the array structure adjustment and the second defect profile curve determined after the array structure adjustment by a formula:

$$PC_F(\theta_m, r_m)=\{P_{Ck}(\theta_k, r_k)\ s.t.\ \theta_m \in R(\theta)\} \cup \{P_{Cj}(\theta_j, r_j)\ s.t.\ \theta_m \notin R(\theta)\}$$

where $PC_F(\theta_m, r_m)$ represents a third defect profile curve obtained after the data fusion and also represents a set of points thereon, m=1, 2, ... M, M is a positive integer and represents a total number of the points on the third defect profile curve;
$P_{Ck}(\theta_k, r_k)$ represents a point on the second defect profile curve, k=1, 2, ..., K, and K is a positive integer and indicates a total number of points on the second defect profile curve;
wherein in the planar polar coordinate system, the second defect profile curve and the function thereof is $PC(\theta_k, r_k)$.

11. A non-transitory computer-readable storage medium having stored therein instructions that, when executed by a processor of a mobile terminal, causes the mobile terminal to perform a method for adjusting an array structure of omnidirectional electromagnetic acoustic transducers for imaging a defect profile of a metal plate, the method comprising:

uniformly arranging N omnidirectional electromagnetic acoustic transducers in a detection region of the metal plate to be detected, wherein each of the omnidirectional electromagnetic acoustic transducers is used as an omnidirectionally emitting electromagnetic acoustic transducer to excite an omnidirectional ultrasonic guided wave in a certain order, and used as an omnidirectionally receiving electromagnetic acoustic transducer to omnidirectionally receive a guided wave scattering signal of a defect when an ultrasonic guided wave is present in the detection region of the metal plate to be detected;

calculating a position of a scattering point according to an amplitude and travel time of the guided wave scattering signal of the defect, and forming a first defect profile curve by performing three smooth spline interpolations on coordinate data of the position of the scattering point;

calculating a curvature of each point on the first defect profile curve in a planar polar coordinate system by solving a first derivative and a second derivative of a function of the first defect profile curve;

determining an array adjustment region by comparing the curvature of the each point with a preset curvature threshold, adjusting the array structure according to the array adjustment region, and calculating a second defect profile curve of the guided wave scattering signal of the defect; and performing data fusion on the first defect profile curve and the second defect profile curve so as to form a defect profile image of the metal plate to be detected.

* * * * *